United States Patent
Nevoigt et al.

(10) Patent No.: US 9,175,270 B2
(45) Date of Patent: Nov. 3, 2015

(54) METHOD OF MODIFYING A YEAST CELL FOR THE PRODUCTION OF ETHANOL

(75) Inventors: Elke Nevoigt, Berlin (DE); Stephane Guillouet, Vallegue (FR); Carine Bideaux, Vernet (FR); Sandrine Alfenore, Castanet-Tolosan (FR); Georg Hubmann, Groningen (NL)

(73) Assignee: Danisco US Inc., Palo Alto, CA (US)

( * ) Notice: Subject to any disclaimer, the term of this patent is extended or adjusted under 35 U.S.C. 154(b) by 929 days.

(21) Appl. No.: 12/740,295

(22) PCT Filed: Oct. 29, 2008

(86) PCT No.: PCT/IB2008/003672
§ 371 (c)(1),
(2), (4) Date: Jun. 28, 2012

(87) PCT Pub. No.: WO2009/056984
PCT Pub. Date: May 7, 2009

(65) Prior Publication Data
US 2012/0295319 A1    Nov. 22, 2012

(30) Foreign Application Priority Data
Oct. 29, 2007    (EP) .................................. 07021129

(51) Int. Cl.
*C12N 9/04*    (2006.01)

(52) U.S. Cl.
CPC ............... *C12N 9/0006* (2013.01); *Y02E 50/17* (2013.01)

(58) Field of Classification Search
CPC ...... C12N 9/0006; Y02E 50/10; Y02E 50/16; Y02E 50/17
See application file for complete search history.

(56) References Cited

U.S. PATENT DOCUMENTS

| | | | |
|---|---|---|---|
| 7,018,829 B1 * | 3/2006 | Nielsen et al. | 435/254.2 |
| 8,110,672 B2 * | 2/2012 | Stephanopoulos et al. | 536/24.1 |
| 2004/0142456 A1 * | 7/2004 | Jeffries et al. | 435/254.21 |
| 2006/0088911 A1 * | 4/2006 | Laplaza et al. | 435/69.1 |
| 2007/0009932 A1 * | 1/2007 | Stephanopoulos et al. | 435/6 |
| 2007/0178505 A1 * | 8/2007 | Fischer et al. | 435/6 |
| 2008/0286870 A1 * | 11/2008 | Viitanen et al. | 435/471 |
| 2009/0053782 A1 * | 2/2009 | Dundon et al. | 435/139 |
| 2009/0311749 A1 * | 12/2009 | Takagi et al. | 435/69.1 |
| 2010/0159546 A1 * | 6/2010 | Aristidou et al. | 435/160 |
| 2010/0291652 A1 * | 11/2010 | Ma | 435/171 |

OTHER PUBLICATIONS

Nissen, T. L., et al., 2000, "Anaerobic and aerobic batch cultivations of *Saccharomyces cerevisiae* mutants impaired in glycerol synthesis", Yeast, vol. 16, No. 5, pp. 463-474.*

Lin, H., et al., 2002 "Phospholipase C interacts with Sgd1p and is required for expression of GPD1 and osmoresistance in *Saccharomyces cerevisiae*", MGG Molecular Genetics and Genomics, vol. 267, No. 3, pp. 313-320.*

Nevoigt, E., et al., 2006,"Engineering of promoter replacement cassettes for fine-tuning of gene expression in *Saccharomyces cerevisiae*", Applied and Environmentalmicrobiology, vol. 72, No. 8, pp. 5266-5273.*

(Continued)

*Primary Examiner* — Manjunath Rao
*Assistant Examiner* — William W Moore
(74) *Attorney, Agent, or Firm* — Danisco US Inc.

(57) ABSTRACT

The invention relates to a method of modifying a yeast cell for the production of ethanol. According to some embodiments of the invention, the activity of the Gpd1 protein and/or the Gpd2 protein is reduced.

7 Claims, 6 Drawing Sheets

(56) References Cited

OTHER PUBLICATIONS

Figure 1:
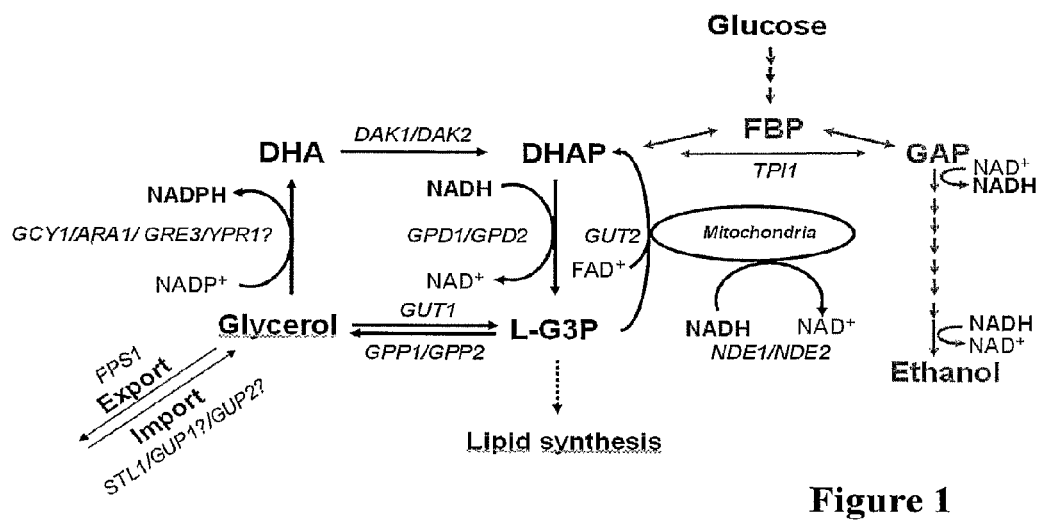

Nevoigt, E., et al. 1997, "Osmoregulation and glycerol metabolism in the yeast *Saccharomyces cerevisiae*", FEMS Microbiology Reviews, vol. 21, pp. 231-241.*

Norbeck, J., et al., 1997, "Metabolic and regulatory changes associated with growth of *Saccharomyces cerevisiae* in 1.4 M NaCl. Evidence for osmotic induction of glycerol dissimilation via the dihydroxyacetone pathway", The Journal of Biological Chemistry, vol. 272, pp. 5544-5554.*

Ansell, R., et al., 1997, "The two isoenzymes for yeast NAD+-dependent glycerol 3-phosphate dehydrogenase encoded by GPD1 and GPD2 have distinct roles in osmoadaptation and redox regulation", EMBO Journal, vol. 16, pp. 2179-2187.*

Anderlund, M., et al., 1999, "Expression of the *Escherichia coli* pntA and pntB genes, encoding nicotinamide nucleotide transhydrogenase, in *Saccharomyces cerevisiae* and its effect on product formation during anaerobic glucose fermentation", Applied and Environmental Microbiology, vol. 65, pp. 2333-2340.*

Nissen, T. L., et al., 2000, "Optimization of ethanol production in *Saccharomyces cerevisiae* by metabolic engineering of the ammonium assimilation", Metabolic Engineering, vol. 2, pp. 69-77.*

Siderius, M., et al., 2000, "The control of intracellular glycerol in *Saccharomyces cerevisiae* influences osmotic stress response and resistance to increased temperature", Molecular Microbiology, vol. 36, pp. 1381-1390.*

Pahlman, A. K., et al., 2001, "The yeast glycerol 3-phosphatases Gpp1p and Gpp2p are required for glycerol biosynthesis and differentially involved in the cellular responses to osmotic, anaerobic, and oxidative stress", The Journal of Biological Chemistry, vol. 276, pp. 3555-3563.*

Nissen, T. L., et al., 2001, "Expression of a cytoplasmic transhydrogenase in *Saccharomyces cerevisiae* results in formation of 2-oxoglutarate due to depletion of the NADPH pool", Yeast, vol. 18, pp. 19-32.*

Bakker, B. M., et al., 2001, "Stoichiometry and compartmentation of NADH metabolism in *Saccharomyces cerevisiae*", FEMS Microbiology Review, vol. 25, pp. 15-37.*

Molin, M., et al., 2003, "Dihydroxyacetone kinases in *Saccharomyces cerevisiae* are involved in detoxification of dihydroxyacetone", The Journal of Biological Chemistry, vol. 278, pp. 1415-14123.*

Oliveira, R., et al., 2003, "Fps1p channel is the mediator of the major part of glycerol passive diffusion in *Saccharomyces cerevisiae*: Artefacts and redefinitions", Biochimica et Biophysica Acta, vol. 1613, pp. 57-71.*

Wojda, I., et al., 2003, "Response to high osmotic conditions and elevated temperature in *Saccharomyces cerevisiae* is controlled by intracellular glycerol and involves coordinate activity of MAP kinase pathways", Microbiology, vol. 149, pp. 1193-1204.*

Rigoulet, M., et al., 2004, "Organization and regulation of the cytosolic NADH metabolism in the yeast Saccharomyces cerevisiae", Molecular and Cellular Biochemistry, vols. 256-257, pp. 73-81.*

Valadi, A., et al., 2004, "Distinct intracellular localization of Gpd1p and Gpd2p, the two yeast isoforms of NAD+-dependent glycerol-3-phosphate dehydrogenase, explains their different contributions to redox-driven glycerol production", The Journal of Biological Chemistry, vol. 279, pp. 39677-39685.*

Nguyen, H. T., et al., 2004, "Engineering of *Saccharomyces cerevisiae* for the production of L-glycerol 3-phosphate", Metabolic Engineering, vol. 6, pp. 155-163.*

Alper, H., et al., 2005, "Tuning genetic control through promoter engineering", Proceedings of the National Academy of Sciences, U.S.A., vol. 102, pp. 12678-12683.*

Granath, K., et al., 2005, "The YIG1 (YPL201c) encoded protein is involved in regulating anaerobic glycerol metabolism in *Saccharomyces cerevisiae*", Yeast, vol. 22, No. 16, pp. 1257-1268.*

Lynd, L. R., et al., 2005, "Consolidated bioprocessing of cellulosic biomass: an update", Current Opinion in Biotechnology, vol. 16, pp. 577-583.*

Bro, C., et al., 2005, "In silico aided metabolic engineering of *Saccharomyces cerevisiae* for improved bioethanol production", Metabolic Engineering, vol. 8, pp. 102-111.*

Lin Y., et al., 2006, "Ethanol fermentation from biomass resources: current state and prospects", Applied Microbiology and Biotechnology, vol. 69, pp. 627-642.*

Hubmann, et al., "Gpd1 and Gpd2 fine-tuning for sustainable reduction of glycerol formation in *Saccharomyces cerevisiae*", Appl Environ Microbiol, 2011, 77:5857-67.

Pagliardini, et al., "Quantitative evaluation of yeast's requirement for glycerol formation in very high ethanol performance fed-batch process", Microb Cell Fact, 2010, 9:36 (1-13). http://www.microbialcellfactories.com/content/9/1/36.

* cited by examiner

```
                      -412
TEF1p unmutated  1.00 + 0.00    ATAGCTTCAAAAATGTTTCTACTCCCTTTTTACTTCTTCCAGATTTTCTCGGACTCCGCGCATCGCCGTACCACTTCAAAAC
Mutant 2         0.07 + 0.01    ACGGCTCTAAAGTGCTTCGGCTCCGCCCCTTTACTCCTCAGTTTTCTCAGACTCCGCGCATCGCCGTACCACTCAAAGC TEF1p unmutated                 ACCCAAGCACAGCAGCATACTAAATTCCCCCTCTTCTTCCTCTAGGTGTCGTTAATTACCCGTACTAAGGTTTGAAAAG
Mutant 2                        CCCCAAGCGCAGCATACCAAATCCAAATCTCCCCCTCTTTCTTCCTCTAGGTGTCACTAGTTACTCGTACTAAGGGTTTGGGAAG TEF1p unmutated                 AAAAAAGAGACCGCCTCGTTTCTCTTTTTCTTCGTCGAAAAAAGGCAATAAAAATTTTTATCACGTTTCTTTTTCTTGAAAAT
Mutant 2                        GAGAAAGAGACCGCCTCGTCGTTGTTTCTTCGTCGAAGGGGCAATAGAAGTTTTTATCATGTCTCCTTTCCTTGAGAAC TEF1p unmutated                 TTTTTTTTGATTTTTTCTCTTTTCGATGACCTCCCATTGATATTTAAGTTAATAAACGGTCTTCAATTTCTCAAGTTTC
Mutant 2                        CTTTTCTTCGATCTTGTTCTCTTTTCGACGGCCCTCCCGTTGGTATTTAGGTTAATGAACGGTCTTCAACCTCAAGTTTC TEF1p unmutated                 AGTTTCATTTTTTCTTGTTCTATTACAACTTTTTTACTTCTTCGTTCATTAGAAAGAAAGCATAGAAAGCAATCTAAACTAAGTTT
Mutant 2                        AGTTTCGTTTGTCCGTCTATTACGACCCTTCTTACTTCTCACTCAGTAGAACGGGAGCATAGCAATCTAATCCAAGTTT

-11
```

Figure 2

METHOD OF MODIFYING A YEAST CELL FOR THE PRODUCTION OF ETHANOL

CROSS-REFERENCE TO RELATED APPLICATION

This application is a National Stage filing of International Application Serial No. PCT/IB2008/003672, filed Oct. 29, 2008, which claims priority to European Patent Application Serial No. 07 021 129.7 filed Oct. 29, 2007, the disclosures of which are expressly incorporated herein by reference.

The invention pertains to a method of modifying a yeast cell, in particular for the production of ethanol. The invention furthermore pertains to a method for producing ethanol from biomass.

Bio-ethanol is a promising alternative to fossil fuels. The increasing interest in renewable biofuels mainly results from the fact that world fossil fuels are limited. Moreover, there is the tendency to decrease the dependency of importing oil. The European Commission has planned to progressively substitute 20% of conventional fossil fuels by alternative fuels in the transport sector by 2020 (5.75% by 2010). One technical pathway is to produce bio-ethanol via microbial fermentation from various domestic crops (biomass).

Bio-ethanol production from sugar and starch containing biomass is common in Brazil and the United States. The yeast *Saccharomyces* (S.) *cerevisiae* has been traditionally used in this process. In fact, the yeast *S. cerevisiae* has outstanding properties for bio-ethanol production. In particular, its high tolerance to the conditions which occur during industrial ethanol production will hardly allow other microorganisms to displace yeast in this field.

Glycerol is formed by *S. cerevisiae* as a by-product during glucose catabolism beside the main fermentation products: ethanol, carbon dioxide and biomass. The carbon flux towards glycerol is quite substantial and can amount up to 0.1 g glycerol per gram glucose (Alfenore et al., 2004; Aldiguier et al., 2004).

Glycerol biosynthesis from the glycolytic intermediate dihydroxyacetone phosphate (DHAP) in *S. cerevisiae* is performed by two enzymatic steps catalyzed by the glycerol 3-phosphate dehydrogenase (GPDH) and the glycerol 3-phosphatase (GPP) (see also FIG. 1). Each enzyme is encoded by two isogenes GPD1/GPD2 and GPP1/GPP2, respectively.

Glycerol biosynthesis has essential roles in *S. cerevisiae*. One of the most important functions is maintaining cytosolic redox balance, especially under anaerobic conditions, and probably also under aerobic conditions when sugar concentration is high (Crabtree effect) (Ansell et al., 1997; Bakker et al., 2001; Rigoulet et al., 2004; Valadi et al., 2004). The glycerol biosynthetic pathway is also involved in the biosynthesis of glycerophospholipids and triacylglycerols which are formed from L-glycerol 3-phosphate (Kohlwein et al., 1996; Mullner and Daum, 2004). In addition, intracellular glycerol is involved in osmoadaptation (Hohmann, 2002), oxidative stress protection (Pahlman et al., 2001), and response to heat shock (Siderius et al., 2000). Responses to elevated temperatures and high osmolarity involve several signaling pathways including the protein kinase C pathway and the HOG pathway, which regulate intracellular levels of glycerol (Hohmann, 2002; Wojda et al., 2003).

In theory, the redirection of carbon flux in *S. cerevisiae* towards the ethanol synthetic pathway by eliminating glycerol formation could increase the ethanol yield by at least 10%. Moreover, reduction of glycerol in the fermentation broth would lead to a decrease in ethanol extraction costs as glycerol has caused problems in the distillation units and separation processes after the fermentation stage. In addition, waste volumes would be reduced. Under practical aspects, however, reducing glycerol formation without negatively affecting the cells' fitness is extremely challenging due to the various biological functions of the glycerol biosynthetic pathway, as will now be outlined with reference to previous studies.

The first metabolic engineering approach to reduce glycerol was reported a few years ago (Nissen et al., 2000a). Ethanol yield in aerobic batch fermentations was increased by 12% when glycerol formation was completely abolished by deleting GPD1 and GPD2. Growth of this double mutant was severely affected even in the presence of oxygen. Therefore, the volumetric ethanol productivity obtained with this approach was far from industrial relevance. The fact that the growth of the gpd1Δ gpd2Δ double mutant was strongly impaired has been explained by a limited capacity of respiratory NADH reoxidation (by the external NADH dehydrogenases Nde1p, Nde2p and the mitochondrial L-G3P/DHAP shuttle) (Nissen et al., 2000a) which are the only pathways for reoxidizing excess cytosolic NADH when GPD is absent.

Other attempts to reduce glycerol formation relied on the introduction of bacterial transhydrogenases into yeast. These approaches failed since, on one hand, the *Azotobacter vinelandii* transhydrogenase produced the opposite expected effect (Nissen et al., 2001), and on the other hand, the membrane-bound transhydrogenase from *Escherichia coli* remained localized in the membrane of the endoplasmic reticulum (Anderlund et al., 1999).

A quite successful strategy to improve ethanol yield has been the metabolic engineering of the ammonium assimilation, reducing the NADH production during amino acid biosynthesis (Nissen et al., 2000b). The glycerol yield was reduced by 38% and the ethanol yield increased by 10%. However, for proper function, this approach requires that yeast utilizes ammonium as a source of nitrogen. Industrial media often contain amino acids, a fact which will considerably reduce the success of this approach under industrial relevant conditions.

Recently, an in silico study was carried out using a genome-scale *S. cerevisiae* metabolic model in order to evaluate possible metabolic engineering strategies to improve ethanol yield in *S. cerevisiae* (Bro et al., 2005). These approaches have been designed to prevent the production of excess NADH through biomass synthesis, and hence, reduce the need to produce glycerol. Based on authors' predictions, several approaches should be able to increase ethanol yield by up to 10.4%. One of the predicted strategies was tested in vivo, but in contrast to theory, only resulted in a 3% increase of ethanol yield.

Therefore, the metabolic engineering approaches mentioned above have no or only marginal impact on ethanol productivity under industrially relevant conditions due to the limitations in ethanol yield, growth or medium dependency. Moreover, it remains questionable if the current and predicted approaches would prove successful under high ethanol and thermal stress of industrial fermentations as they do not take into account the cells' need for intracellular glycerol.

DESCRIPTION OF THE INVENTION

The problem underlying the present invention therefore was to increase the conversion yield from fermentable biomass constituents into ethanol by yeast and, in effect, to increase the economic efficiency of bio-ethanol plants. One way to solve this goal is to reduce the production of the by-product glycerol.

A particular challenge in solving this problem lies in the fact that the complete elimination of glycerol formation has proven to be unsuccessful, as the glycerol biosynthetic pathway has several important functions for cell growth and stress tolerance.

Instead, the inventors surprisingly found a strategy for modifying a wild type yeast cell that leads to an increased yield of ethanol from sugars, i.e. fermentable sugars present in hydrolysates of plant biomass, but at the same time does not have a negative influence on the growth rate of the yeast cells or the biomass yield. According to the invention, this is achieved by reducing (but not eliminating) the activity of the Gpd1 protein and/or the Gpd2 protein when compared to the activity of these proteins in a wild-type cell.

In effect, a higher ethanol yield, titer and specific productivity compared to the isogenic wild-type strain is achieved through the invention. Also, the metabolic pathway modification has the additional advantage to lower the costs for product recovery and reduces waste volumes.

The term "reducing the activity" is meant not to include the elimination of the activity of the protein. Moreover, the term "activity" refers to the in vivo metabolic flux through the particular protein, which, according to the definition of the term "reducing the activity" is not meant to include the complete blockage of this metabolic flux. Instead, the crux of the invention lies in the reduction of the activity of the Gpd1 protein and/or the Gpd2 protein, but at the same time providing a minimum activity of Gpd1 protein and/or the Gpd2 protein in order to allow for the production of substances downstream of these enzymes (such as glycerol) that are necessary to maintain a normal growth rate.

This result can be achieved in different ways: First, it is possible to reduce the activity of the Gpd1 protein and to eliminate the activity of the Gpd2 protein. Secondly, the activity of the Gpd1 protein can be eliminated and the activity of the Gpd2 protein can be reduced. Thirdly, the activity of both the Gpd1 protein and the Gpd2 protein can be reduced. Which of the three options leads to best results depending e.g. on the type of yeast strain used or the growth conditions can be determined by a person of skill in the art without undue burden.

The yeast cells according to the invention are useful for any application in which the production of glycerol in the cell needs to be minimized to a level that does not negatively influence the growth rate of the cell.

The reduction of the activity of the Gpd1 protein and/or the Gpd2 protein can be achieved in several ways that will now be outlined (under a) to e)). It lies within the inventive concept that one or a combination of the given possibilities can be used for a reduction in protein activity.

a) One way is to reduce the expression of the GPD1 gene and/or the GPD2 gene, which leads to a reduction of the protein in the cell.

This can be achieved in one embodiment of the invention by expressing the GPD1 gene and/or the GPD2 gene by a weak promoter that is operably linked to the GPD1 gene and/or operably linked to the GPD2 gene. A promoter is weak when the transcription rate of the gene is reduced to at least 20% or 15%, preferably to at least 10%, most preferably to at least 7% or 5% of the transcription rate of that gene expressed under the TEF1 wild type promoter (SEQ ID NO 11). Ways of measuring the strength of a promoter are known to a person of skill in the art, such as using a reporter gene like luciferase or green fluorescent protein (GFP), measuring the mRNA levels, e.g. using Northern blot or real-time reverse transcriptase PCR; on the protein level by Western blotting; or through measurements of the specific enzyme activity.

It is preferred that the expression of the GPD1 gene and/or the GPD2 gene is reduced by at least 50%, at least 60%, or at least 70% compared to its expression in a wild type cell under its wild type promoter. It is of particular advantage to reduce expression by at least 80%, or at least 90%, and it is most preferred to reduce the expression by at least 95%, or at least 99%, compared to the expression of the particular gene in a wild type yeast cell, i.e. a yeast cell with a native promoter.

In a preferred embodiment, the weak promoter is a promoter according to SEQ ID NO 5 or 6. The promoter according to SEQ ID NO 5 leads to a transcription rate of 7% and the promoter according to SEQ ID NO 6 leads to a transcription rate of 16% of the transcription rate caused by the TEF1 wild type promoter (SEQ ID NO 11) (Nevoigt et al., 2006).

b) The reduction of the activity of the Gpd1 protein and/or the Gpd2 protein can also be achieved by providing or expressing an antisense molecule, such as an RNA molecule, to the GPD1 and/or the GPD2 mRNA to impede translation of the mRNA into a protein.

It is preferred that the antisense molecule has a sequence that hybridizes with the mRNA according to SEQ ID NO 1 or 2. In another embodiment, the antisense molecule hybridizes with or is reverse complementary to any 10 to 30 bases, preferably to any 18 to 23 bases of the mRNA according to SEQ ID NO 1 or 2.

When using antisense molecules, it is generally preferred to design them against untranslated regions of the mRNA.

Another possible means of reducing the activity of the Gpd1 protein and/or the Gpd2 protein are ribozymes, which can catalytically cleave the gpd1 and/or the gpd2 mRNA.

Several approaches have been developed based on antisense molecules and ribozymes to regulate gene expression, such as riboswitches. Riboswitches contain aptamer domain sites comprising highly specific pockets in the 5' untranslated region of the mRNAs that bind small molecules or ligands. Upon binding of a ligand to an aptamer site a conformational change in the RNA structure leads to a change in gene expression.

Moreover, it is possible to target transcription factors to lower the transcription rate of the Gpd1 protein and/or the Gpd2 protein. It has, e.g. been described that overexpression of Yig1p leads to a decreased activity of GPP (Granath et al, 2005).

c) Alternatively, the reduction of the activity of the Gpd1 protein and/or the Gpd2 protein can also be achieved by providing or expressing a functional antagonist to the Gpd1 and/or the Gpd2 protein, that functionally inhibits the enzymatic activity of the respective protein.

d) Also, the reduction of the activity of the Gpd1 protein and/or the Gpd2 protein can be achieved by providing or expressing a mutated form of the Gpd1 and/or the Gpd2 protein.

Such a mutant exhibits a functional inhibition of the enzymatic activity that can bear a mutation in a functional domain of the protein, such as the active center or a binding or recognition domain and leads to a reduced enzymatic activity of the respective protein without abolishing its function.

e) Finally, the reduction of the activity of the Gpd1 protein and/or the Gpd2 protein can also be achieved by providing a small inhibitory molecule for inhibiting the Gpd1 and/or the Gpd2 protein.

The amino acid sequences of the Gpd1 protein, the Gpd2 protein, the Gpp1 protein, and the Gpp2 protein from *S. cerevisiae* can be found as SEQ ID NO 26, 27, 28, and 29, respectively. For other yeast species, a person of skill in the art can identify the respective amino acid sequence.

In a preferred embodiment of the method according to the invention, the Gpp1 protein and/or the Gpp2 protein, i.e. another key enzyme of the glycerol pathway, is also reduced in its activity in addition to the activity reduction of the Gpd1 protein and/or the Gpd2 protein.

It is possible either to reduce the activity of the Gpp1 and eliminate the activity of the Gpp2 protein, to eliminate the activity of the Gpp1 and reduce the activity of the Gpp2 protein, or to reduce both the activity of the Gpp1 and of the Gpp2 protein. In addition, it is also possible to eliminate both the activity of the Gpp1 and of the Gpp2 protein in one embodiment, as will be shown in the examples.

The means that can be used for reducing the activity of the Gpd1 protein and/or the Gpd2 protein are equivalent to the means explained above and apply in an equivalent fashion also for the activity reduction of Gpp1 and/or Gpp2, as will be realized by a person of skill in the art. Accordingly, the GPP activity can be reduced by reducing the expression of the Gpp1 and/or the Gpp2 protein, by providing an antisense molecule to the GPP1 (SEQ ID NO 3) and/or the GPP2 mRNA (SEQ ID NO 4), by providing an antagonist to the Gpp1 and/or the Gpp2 protein, by providing a mutated form of the Gpp1 protein and/or the Gpp2 protein or by providing a small inhibitory molecule such as fluoride, which has been described as an unspecific inhibitor of phosphatases, for inhibiting the Gpp1 protein and/or the Gpp2 protein. For details regarding these reduction means, reference is made to the description given above.

The present invention can generally be used with any yeast strain, such as *S. cerevisiae* and closely related species (i.e. other species of the genus *Saccharomyces*). Other Non-*Saccharomyces* yeast species, especially those which show ethanolic fermentation and have the ability to ferment pentoses such as *Pichia* (P.) *stipitis*, are also preferred. It is particularly preferred to use strains that are advantageous in industrial applications, such as the prototrophic *S. cerevisiae* yeast strain CEN.PK113-7D. Other suitable strains are known to a person of skill in the art.

It will be understood by a person of skill in the art that when using a diploid or polyploid strain, it becomes necessary to reduce the activities of the Gpp1p and/or Gpp2p as well as possibly Gpd1p and/or Gpd2p in all of the alleles present in order to achieve the necessary reduction in protein activity.

The underlying problem is also solved by a yeast cell, in particular a genetically modified yeast cell that is obtainable through a method as described above.

Specifically, in such a yeast cell, the activity of the Gpd1p and/or Gpd2p protein is reduced in comparison to the activity of said proteins in a wild-type yeast cell, i.e. in a yeast cell with a normal protein activity (normal flux) and a normal growth rate, or, put differently, in comparison to a yeast cell in which the modifications present in the genetically modified yeast cell according to the invention that lead to the reduced activity of the Gpd1 and/or Gpd2 protein are not present.

For the preferred amount of reduction of protein activity, reference is made to the description above.

Means for reducing the activity of said proteins were described above, the application of which leads to a yeast cell in which
- the expression of the GPD1 gene and/or gpd2 gene is reduced,
- an antisense molecule to the GPD1 and/or gpd2 mRNA, e.g. in the form of an RNA molecule, is present,
- a functional antagonist to the Gpd1 protein and/or Gpd2 protein is present,
- a mutated form of a Gpd1 protein and/or Gpd2 protein, that is functionally inhibited is present, and/or
- a small inhibitory molecule for inhibiting the Gpd1 and/or the Gpd2 protein is present.

Further characteristics of such a yeast cell according to the invention were described above in relation to the method according to the invention.

The underlying problem is also solved through the use of a yeast cell, in particular a genetically modified yeast cell as describe above for producing ethanol from biomass. This can be achieved by providing a modified yeast cell as described above, providing biomass and growing the yeast cell in the presence of the biomass, as well as obtaining the ethanol. In general, the yeast cells according to the invention can be used in any application in which high glycerol production in the cell is to be avoided, since the reduction of glycerol according to the method described here does not lead to smaller growth rates.

The term biomass when used together with a method of producing ethanol, is meant to refer to plant and plant-derived materials, such as starch, sugar, cellulose, hemicellulose, in particular from sugar cane, sugar beet, corn, grain, etc.

The underlying problem is furthermore solved by a method for the production of ethanol which comprises the following steps:
- providing a yeast cell as described above,
- providing biomass, and
- growing the yeast cell in the presence of the biomass under conditions that allow for the production of ethanol.

As will be evident to a person of skill in the art, it might be necessary or advantageous to treat the biomass chemically, enzymatically or mechanically prior to growing the yeast together with the biomass in order to facilitate fermentation. Methods for such treatments are known to a person of skill in the art.

As shown by Alfenore et al., 2004, the production of glycerol can also be reduced by adapting the growth conditions of the yeast cell. Particularly the aeration conditions and the composition of the medium can have a large influence on glycerol production and therefore on ethanol production.

FIGURES

FIG. 1

The pathways involved in glycerol metabolism in *Saccharomyces cerevisiae* are shown. Glycerol is formed from glycolytic dihydroxyacetone phosphate (DHAP) by the action of both glycerol-3-phosphate dehydrogenase (GPD encoded by GPD1 and GPD2) and glycerol-3-phosphatase (G3Pase encoded by GPP1 and GPP2). Gut1p and Gut2p are responsible for the utilization of glycerol. The pathways for biosynthesis and metabolization of glycerol in *S. cerevisiae* have been reviewed by Nevoigt and Stahl (1997). The Fps1p channel is the mediator of the major part of glycerol passive diffusion (Oliveira et al., 2003). Yeast cells take in glycerol via transporter Stl1p and probably also via Gup1p and Gup2p (Ferreira et al., 2005). Glycerol is converted to dihydroxyacetone (DHA) by NADP+-dependent glycerol dehydrogenase (GDH). The genes ARA1, GCY1, GRE3, YPR1 are suggested to contribute to this activity (Izawa et al., 2004); however, others reported that no activity of this enzyme at all is detectable, a result which has put the relevance of the DHA pathway for *S. cerevisiae* into question (Norbeck and Blomberg, 1997). DAK1 and DAK2 encode dihydroxyacetone kinase (Molin et al., 2003). NDE1 and NDE2 encode the external NADH dehydrogenase in yeast which is able to directly reoxidize cytosolic NADH transferring the electrons to the respiratory chain. DHAP: dihydroxyacetone phosphate, GAP: glyceraldehyde 3-phosphate, L-G3P: L-glycerol 3-phosphate, DHA: dihydroxyacetone, FBP: 1,6-fructose bisphosphate, and the TPI1: gene encoding triose phosphate isomerase

FIG. 2

FIG. 2 shows the sequence alignment of the unmutated TEF1 promoter of *Saccharomyces cerevisiae* and TEF1 promoter mutant 2. The normalized promoter strength is shown.

FIG. 3

Specific activity of glycerol 3-phosphate dehydrogenase of the engineered *Saccharomyces cerevisiae* strain related to the isogenic wild type. 1 Unit is defined as the conversion of 1 µmole of substrate per minute and mg protein.

FIG. 4

Ethanol, biomass and glycerol yields in gram per glucose consumed of the engineered *Saccharomyces cerevisiae* strain and the isogenic wild type after depletion of glucose in fermentations of YEPD medium under oxygen-limited conditions.

FIG. 5

The result of a growth experiment of the engineered *Saccharomyces cerevisiae* strain and the isogenic wild type on YEPD medium (agar-plates) under aerobic and anaerobic conditions is shown.

FIG. 6

The result of a growth experiment of the engineered *Saccharomyces cerevisiae* strain and the isogenic wild type in liquid YEPD medium under aerobic conditions is shown.

FIG. 7

Ethanol, glycerol production and sugar consumption after batch fermentation under oxygen-limited conditions at 30° C. in wheat mash. Wheat mash was completely saccharified and centrifuged before fermentation was started. The hydrolysate contained roughly 143 g/l total sugar, i.e. glucose and fructose. Oxygen-limited conditions were obtained by closing the Erlenmeyer flasks with air-locks which allowed the release of gases. Mixing was carried out using a magnetic stirrer set at 200 rpm. For this experiment, the prototrophic *S. cerevisiae* yeast strain CEN.PK113-7D and a derivative deleted in GPD2 and carrying modifications of the GPD1 promoter (a TEF1 promoter mutant version (mutant promoter 2, SEQ ID NO 5) and the loxP-KmR-loxP sequence as a selectable marker) was used. The genes encoding GPP1 and GPP2 were not modified in this strain.

In all panels A to F of FIG. 7, the left bar shows: CEN.PK113-7D, 100% GPD activity, and the right bar shows CEN.PK113-7D, 6% GPD activity.

The y-axis of the panels is as follows:

| | |
|---|---|
| 7A | Final glycerol concentration (g/l) |
| 7B | Final ethanol concentration (g/l) |
| 7C | Glycerol yield (g/g glucose, fructose consumed) |
| 7D | Ethanol yield (g/g glucose, fructose consumed) |
| 7E | Ration: glycerol/ethanol (g/g) |
| 7F | Sugar (glucose, fructose) consumed (g/l) |

EXAMPLES

Material and Methods

Media:

YEPD medium (1% yeast extract, 2% peptone, 2% glucose)

Yeast Strains:

The yeast strains generated in this study originate from *S. cerevisiae* laboratory strain W303-1A (Table 1). The strain YA103 corresponding to a gpp1Δ gpp2Δ double deletion strain has been published by Pahlman et al. (2001).

Further Genetic Modifications of *S. cerevisiae* Strain YA103:

1. Deletion of GPD2 Gene/Abolishment of GPD2 Expression

The GPD2 gene was disrupted in the strain YA103 by the method described by (Guldener et al., 1996) using pUG72 (Gueldener et al., 2002) as a template and the primers P29 and P30 (Table 2). Disruption of GPD2 was checked by diagnostic PCR using the primer pair P33/P34 (Table 2). Selection of positive transformants was carried out on agar plates containing CSM-medium lacking uracil. The resulting strain has been referred as to EN-GGG (Table 1).

2. Down-Regulation of GPD1 Expression

The native chromosomal GPD1 promoter in the strain EN-GGG was replaced by the promoter replacement cassette amplified from genomic DNA of a yeast strain derived from laboratory yeast BY4741 bearing the mutated TEF promoter with the lowest activity (Nevoigt et al., 2006) in place of the native GPD1 promoter. The primers P9 (SEQ ID NO 7) and P10 (SEQ ID NO 8) were used for PCR amplification of the promoter replacement cassette (including the loxP-K.l.LEU2-loxP sequence as a selectable marker). PCR conditions were as previously published (Nevoigt et al., 2006). Two 100 µl PCR aliquots were combined, precipitated used for transformation as described by Güldener et al. (1996). Selection of positive transformants was carried out on agar plates containing CSM-medium lacking leucine.

Correct integration of the promoter replacement cassette was checked by diagnostic PCR using primer combination P9 (SEQ ID NO 7)/P12 (SEQ ID NO 10) and P11 (SEQ ID NO 9)/P12 (SEQ ID NO 10) (Table 2). The resulting strain has been referred as to EN-G46a (Table 1).

TABLE 1

*S. cerevisiae* strains used in the examples

| Strain | Genotype | Reference |
|---|---|---|
| W303-1A* | MATa | Thomas and Rothstein (1989) |
| YA103* | MATa gpp1Δ::kanMX4 gpp2Δ::HIS3 | |
| EN-GGG* | MATa gpp1Δ::kanMX4 gpp2Δ::HIS3 gpd2Δ::K.l.URA3 | Påhlman et al. (2001) |
| EN-G46a* | MATa gpp1Δ::kanMX4 gpp2Δ::HIS3 gpd2Δ::K.l.URA3 gpd1p::TEFmut2::K.l.LEU2 | |

*These strains harbor additional mutations as follows; leu2-3/112 ura3-1 trp1-1 his3-11/15 ade2-1 can1-100 GAL SUC2 mal0

TABLE 2

Primers used

| Use/name | Sequence | SEQ ID NO |
|---|---|---|

Amplification of the promoter replacement cassette including the TEF1 promoter mutant version (mutant promoter 2 described in Nevoigt et al., 2006) and the loxP-K.1.LEU2-loxP sequence as a selectable marker:

| | | |
|---|---|---|
| P9 (binds upstream GPD1 prom.) | cccaaggcaggacagttacc | SEQ ID NO 7 |
| P10 (binds in GPD1 cod. seq.) | agcaccagatagagcaccaca | SEQ ID NO 8 |

Diagnostic PCR to check the correct integration of the promoter replacement cassette:

| | | |
|---|---|---|
| P11 (binds in K.1.LEU2) | ggaccaccaacagcacctagt | SEQ ID NO 9 |
| P12 (binds downstream integration site in GPD1 coding sequence) | gtaagcaactgttgtttcaga | SEQ ID NO 10 |

Deletion of GPD2 using loxP-K.1.URA3-loxP as a selectable marker:

| | | |
|---|---|---|
| P29 | atgcttgctgtcagaagattaacaagatacacattcctt agatcccaatacaacagatcacg | SEQ ID NO 12 |
| P30 | cgatgtctagctcttcaatcatctccggtaggtcttcca tgttttatttaggttctatcg | SEQ ID NO 13 |

Diagnostic PCR to check the disruption of GPD2:

| | | |
|---|---|---|
| P33 | ggtagattcaattctctttccc | SEQ ID NO 14 |
| P34 | aggcaacaggaaagatcagagg | SEQ ID NO 15 |

Oxygen-Limited Batch-Fermentations and Determination of Product Yields

1st Day:
  $1^{st}$ pre-culture: inoculate 20 ml YEPD with 500 µl glycerol stock
  Incubate over night at 30° C. at a shaker (170 rpm) for 20 hours 2nd Day:
  2nd preculture: inoculate 150 ml YEPD with 1.5 ml of the first preculture
  Incubate over night at 30° C. at a shaker (170 rpm) for 20 hours 3rd Day:
  Centrifuge 2nd preculture (10 min, 5000 rpm, 4° C.) and wash the cells once with destilled water
  Inoculation of main culture: inoculate 100 ml YEPD in 100 ml—Schott flasks by adjusting an OD of 0.2
  Immediately, samples were taken for determination of initial concentrations of glycerol, ethanol, glucose and biomass
  Add a magnetic stirrer and close the flasks with air locks to ensure release of gases but prevent oxygen intake
  Stir the culture for 24 h at 28° C. and 300 rpm 4th Day:
  Samples (2×1 ml) were taken, centrifuged (10 min, 12000 rpm, 4° C.) and the supernatants were stored at −20° C. until glycerol, ethanol and glucose concentrations were measured. The measurements of glucose and fermentation products were carried out as previously described (Nevoigt and Stahl, 1996). Yeast dry weight (biomass) at the end of fermentation was determined by filtering 30 ml of the culture using pre-weighted nitrocellulose filters (pore size 0.45 mm). The filters with the cells were washed with distilled water and dried until the weight reached a stable value.

Determination of Specific Activity of Glycerol 3-Phosphate Dehydrogenase

In vitro enzyme activities were, in general, determined during logarithmic growth, i.e. when cell density was about 1 during the batch fermentations. Yeast cells were broken by vortexing with glass beads (0.5 mm in diameter) for 15 min at 4° C. in accordance with a previously described method (Ciriacy, 1975). In order to assay GPD, approximately $3 \times 10^9$ cells were harvested and homogenized in 3 ml triethanolamine buffer (Blomberg and Adler, 1989; Andre et al., 1991) containing 0.2 mmol/l-phenylmethyl-sulphonylfluoride and 2 g glass beads. The homogenate was centrifuged in each case at 12 000 g and 4° C. for 15 min. The supernatant was used after desalting by passage through a Sephadex G-25 column. (Pharmacia PD-10, Pharmacia Fine Chemicals, Sweden). GPD was assayed in imidazole buffer at pH 7.0 in accordance to Gancedo et al. (1968). Protein concentration was measured by the Coomassie blue method (Bradford, 1976), using bovine serum albumin A 3350 (Sigma Chemical Co., St Louis, Mo.) as a standard (Nevoigt and Stahl, 1996).

Growth on Agar Plates Under Aerobic and Anaerobic Conditions

Stationary phase cultures of the two strains in YEPD medium were diluted (decadal dilutions) and an aliquot was transferred to YEPD agar plates using a stamp. Plates were incubated for 3 days. Oxygen-free conditions were obtained by applying Anaerocult A (MERCK) in an airtight incubator.

Deletions of GPP1 and GPP2

Deletion of the GPP1 gene can be accomplished by the long flanking homology PCR targeting technique (Pahlman et al, 2001). In the first step, a set of primers (TGTGTGAGT-TCCTCTTTTCTT (SEQ ID NO 16) and TCAAAGGCAT-TGCGATGGTT (SEQ ID NO 17)) was used to amplify a 263 base pair (bp) long portion of genomic DNA from S. cerevisiae W303, upstream from the third codon in the GPP1 ORF. A second set (CGCTAAGGATGACTTGTTGA (SEQ ID NO 18) and CTCTAACTTCTCGTCGTACT (SEQ ID NO 19)) was used to amplify a 358 bp fragment from the ninth codon in the GPP1 ORF upstream the stop codon. The 59-end of the primers adjacent to the insertion site carried 25 nucleotide extensions homologous to the 59 and 39 regions of the his-GMX6 or kanMX4 disruption cassette of plasmid pFA6a-hisGMX6 and pFA6-kanMX4. In the second PCR reaction, pFA6a-hisGMX6 and pFA6-kanMX4 were used as templates and the 59 and 39 homologous regions of the first PCR reaction were fused to the disruption cassette by serving as primers together with the upstream forward and downstream reverse primers of the flanking regions, thus producing the ORF targeting cassette. This cassette was transformed into a haploid *S. cerevisiae* W303 strain, and independent transformants were selected for verification of GPP1 replacement. Using a set of primers (forward: CAAGCAGGAAATCCG-TATCA (SEQ ID NO 20) and reverse TCATATGGAG-CAATCCCACT (SEQ ID NO 21)) hybridizing upstream and downstream, respectively, of the disruption cassette chromosomal DNA was amplified. The length of the PCR products was verified by agarose-gel electrophoresis. The GPP2 ORF was disrupted in a similar way using a set of primers (CAAGTGAGGACTTTTCGGAT (SEQ ID NO 22) and GTAGTCAATCCCATTCCGAA (SEQ ID NO 23)) to amplify a 346-bp fragment upstream from the fourth codon in the ORF. The second set (GGACGATCTGTTGAAATGGT (SEQ ID NO 24) and CCTGTCCACTTTCAAGTTGCT (SEQ ID NO 25)) was used to amplify a 287-bp fragment from the seventh codon in the GPP2 ORF downstream the stop codon. Correct integration of the disruption modules into the GPP1 and GPP2 alleles was verified by PCR using appropriate primers.

Based on this strain, further deletions were introduced as described herein.

Preliminary Experiments

In initial studies, the inventors tested strains deleted in GPP for their ability to prevent glycerol formation in fuel bio-ethanol production. The complete elimination of GPD, a key enzyme in glycerol biosynthesis, was not straightforward. The main advantages of abolishing GPP activity, instead of GPD, have been seen in i) keeping the NADH reoxidizing step of glycerol biosynthesis (fulfilled by gene products of GPD1/2), and ii) providing L-G3P for anabolic purposes (FIG. 1).

Both single deletion strains (gpp1Δ and gpp2Δ) and a double deletion strain (gpp1Δgpp2Δ) of the laboratory yeast strain W301-1A were studied. The phenotypes of the different strains were characterized during dynamic ethanol fermentation processes in a highly instrumented bio-reactor in mineral medium under aerobic conditions. Comparative analysis of the wild-type strain and the different mutant strains led to the following conclusions:
- a single deletion of one of the two GPP genes did not lead to important phenotypic changes (growth, ethanol and glycerol production)
- the glycerol concentration was only decreased by 65% in the double deletion mutant gpp1Δ gpp2Δ but not abolished
- the gpp1Δ gpp2Δ double mutant showed a negatively affected growth rate (decreased by 65%) and a lower ethanol tolerance The pathway of glycerol formation in a gpp1Δ gpp2Δ mutant is unknown. Moreover, the reasons for negatively affected growth and the lower ethanol tolerance in the double deletion mutant gpp1Δ gpp2Δ remain unclear. Nevertheless, data shows that complete deletion of GPP is also not straightforward to strongly improve ethanol productivity. GPP likely has another unknown but important function in the cell.

Our experiments show that growth of a gpp1Δ gpp2Δ mutant can be recovered to wild-type level after reducing GPD activity in this strain. It is therefore assumed, without wanting to be bound to theory, that a high intracellular accumulation of L-glycerol 3-phosphate is responsible for the growth defect of a gpp1Δ gpp2Δ mutant. This high level is reduced when GPD activity is reduced in the cell.

Hence, the inventors surprisingly found that cell fitness is maintained (in GPP wild-type) or restored (in cells with abolished GPP activity) if the activity of GPD, a key enzyme in the glycerol biosynthetic pathway is not completely abolished, but instead a minimal flux through the key enzyme required by the cell is maintained. This is in contrast to complete abolishment of GPD or GPP, as both proved to be detrimental for cell fitness.

Generation of Promoters of Graded Activities for Fine-Tuning Enzyme Activities

It is of crucial importance to have tools for fine-tuning enzyme activities in order to determine cells' minimal requirements with regard to the flux through the glycerol biosynthetic pathway. Recently, a robust and well-characterized collection of yeast promoter mutants of finely graded strengths was developed (Alper et al., 2005; Nevoigt et al., 2006). Using these promoter mutants, promoter replacement cassettes were created, which are now available in combination with two different genetically selectable markers. To show the utility of these promoter cassettes, they have been used to tune GPD1 expression in *S. cerevisiae* and analyze the impact on glycerol formation and biomass yield (Nevoigt et al., 2006).

Results

A *S. cerevisiae* laboratory strain was generated which carries deletions in the genes GPP1, GPP2 and GPD2 and which has a very low expression of GPD1 due to the fact that the native GPD1 promoter in the yeast genome was replaced by a weak promoter. This weak promoter (SEQ ID NO 5) was obtained from the TEF1 promoter mutant collection (TEFp mutant 2) created by Nevoigt et al. (2007) and is shown together with the TEF1 wild type promoter (SEQ ID NO 11) in FIG. 2.

Figure 3:
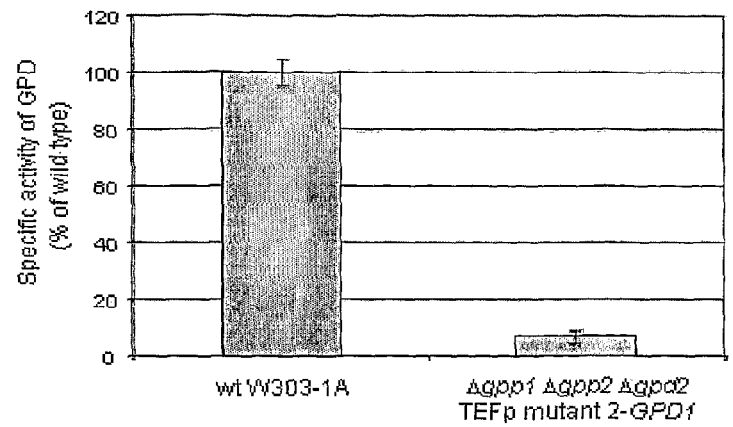
Figure 4:
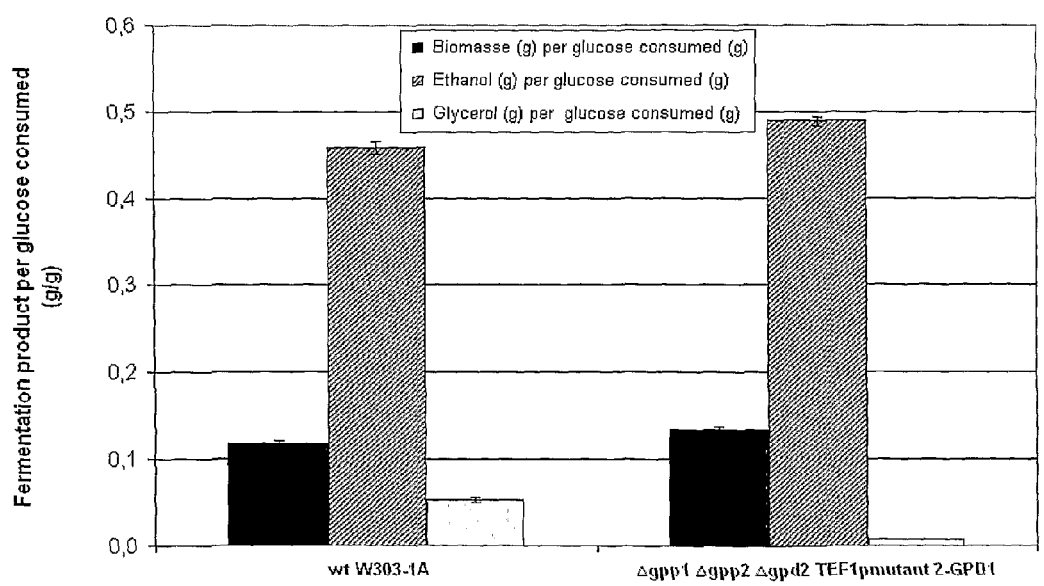
Figure 5:
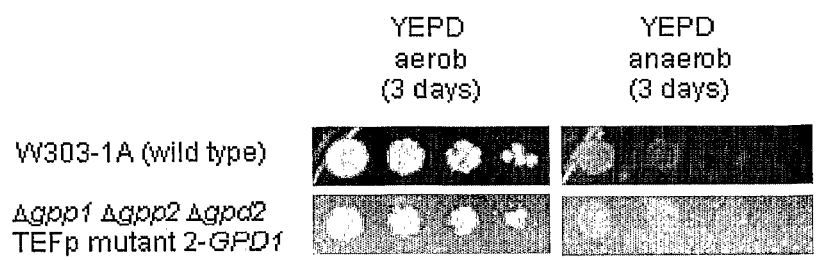
Figure 6:
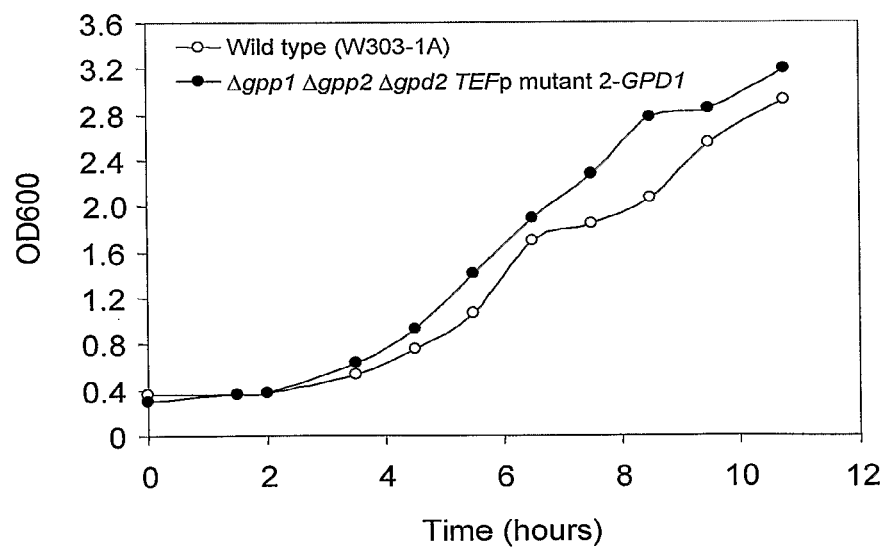
Figure 7B:
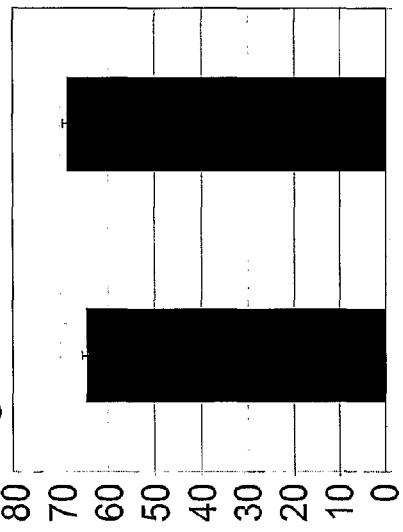
Figure 7D:
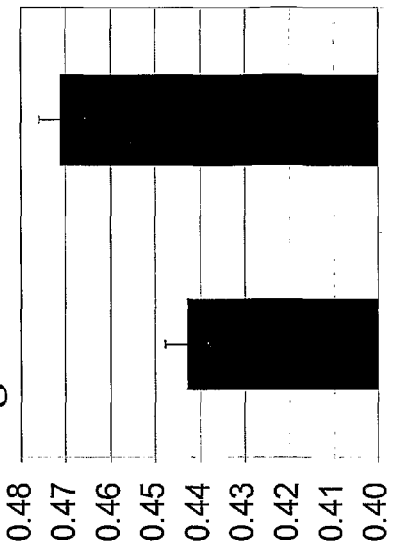
Figure 7A:
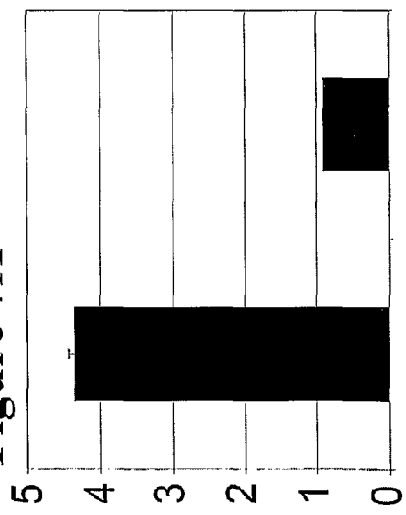
Figure 7C:
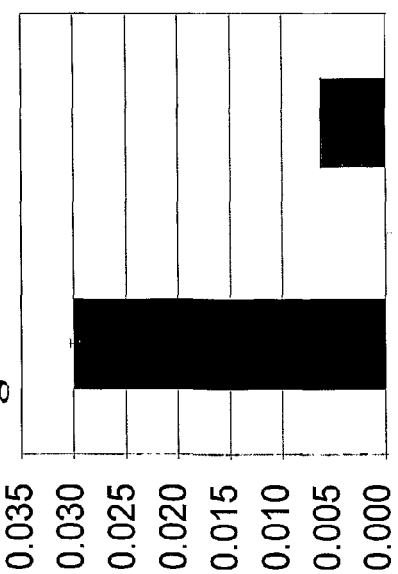
Figure 7E:
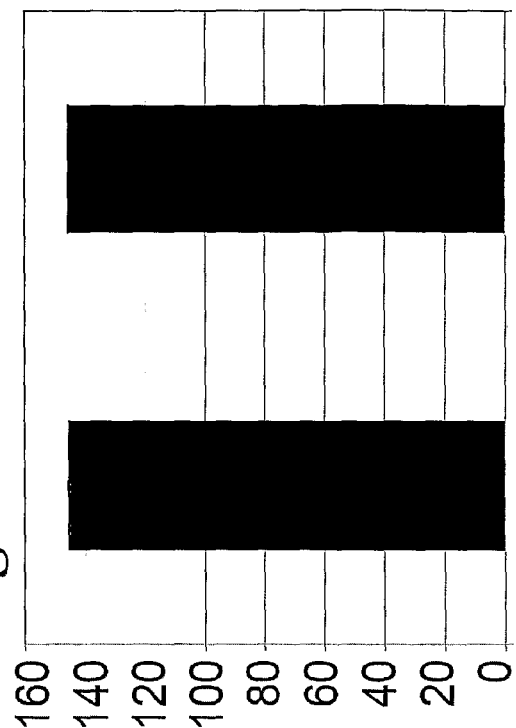
Figure 7F:
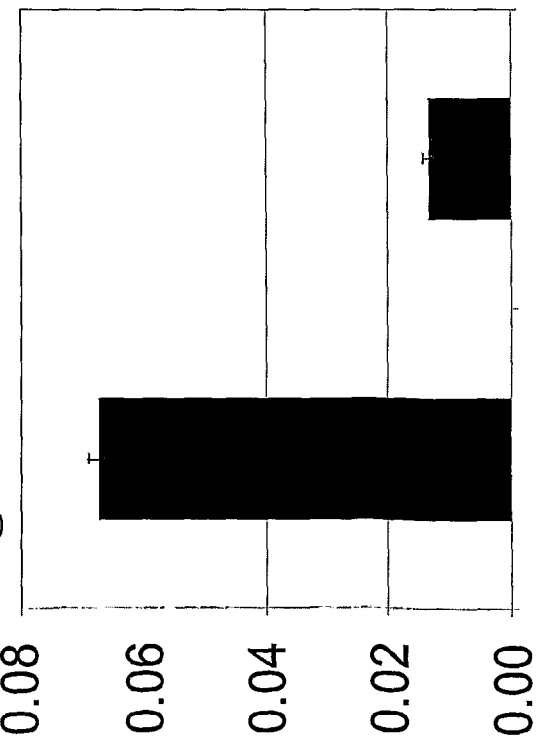

This strain referred to as gpp1Δgpp2Δ gpd2Δ TEF1pmut2-GPD1 (EN-G46a; Table 1) showed a GPD activity which was about 7% that of the isogenic wild type (FIG. 3). The gpp1Δ gpp2Δ gpd2Δ TEF1pmut2-GPD1 and the corresponding wild type were used to ferment 2% glucose in a complex medium (YEPD) under oxygen limiting conditions (see Methods above). The engineered strain showed a glycerol yield per gram glucose consumed which was only 14.5% that of the wild type (FIG. 4). The ethanol yield (gram ethanol per gram glucose consumed) was 6.7% higher than the wild type yield (FIG. 4). Surprisingly, the final biomass yield (FIG. 4) was not influenced by the engineering of the glycerol pathway even though the conditions during the batch fermentation were quasi anaerobic (100 ml culture in 100 ml flasks closed with air-locks). The growth of both strains under aerobic and anaerobic conditions was also investigated using YEPD agar plates and there was virtually no difference (FIG. 5). The growth in liquid YEPD medium under aerobic conditions was also shown to be the same (FIG. 6). Both strains showed an average growth rate of 0.27 $h^{-1}$ during exponential growth phase.

Preliminary experiments have shown that the same result can be obtained by down-regulating GPD activity alone, i.e. without GPP1 and GPP2 deletions. Therefore, it seems that the deletions of GPP1 and GPP2 are not necessary for the invention.

INDUSTRIAL RELEVANCE OF THE RESULTS

The results obtained have a great impact on bio-ethanol production (including biofuels of the first generation) as more ethanol can be produced from the same amount of substrate (carbohydrates such as hydrolysates of starch, cellulose or hemicellulose). Moreover, glycerol production is strongly reduced. This is also important because glycerol participates to the fouling of the distillation units in bio-ethanol production process.

This is the first time that glycerol production was strongly reduced without negatively influencing growth under oxygen limiting conditions. The increase in ethanol productivity is higher than described in the prior art due to the normal growth rate of the cells together with an increased production of ethanol at the expense of glycerol formation.

REFERENCES

Alfenore, S., Cameleyre, X., Benbadis, L., Bideaux, C., Uribelarrea, J. L., Goma, G., Molina-Jouve, C. and Guillouet, S. E. (2004). Aeration strategy: a need for very high ethanol performance in Saccharomyces cerevisiae fed-batch process. Appl Microbiol Biotechnol 63, 537-42.

Alper, H., Fischer, C., Nevoigt, E. and Stephanopoulos, G. (2005). Tuning genetic control through promoter engineering. Proc Natl Acad Sci USA 102, 12678-83.

Anderlund, M., Nissen, T. L., Nielsen, J., Villadsen, J., Rydstrom, J., Hahn-Hagerdal, B. and Kielland-Brandt, M. C. (1999). Expression of the Escherichia coli pntA and pntB genes, encoding nicotinamide nucleotide transhydrogenase, in Saccharomyces cerevisiae and its effect on product formation during anaerobic glucose fermentation. Appl Environ Microbiol 65, 2333-40.

Andre L, Hemming A, Adler L. 1991. Osmoregulation in Saccharomyces cerevisiae. Studies on the osmotic induction of glycerol production and glycerol-3-phosphate dehydrogenase (NAD+). FEBS Lett 286(1-2):13-7.

Ansell, R., Granath, K., Hohmann, S., Thevelein, J. M. and Adler, L. (1997). The two isoenzymes for yeast NAD+-dependent glycerol 3-phosphate dehydrogenase encoded by GPD1 and GPD2 have distinct roles in osmoadaptation and redox regulation. Embo J 16, 2179-87.

Bakker, B. M., Overkamp, K. M., van Maris, A. J., Kotter, P., Luttik, M. A., van Dijken, J. P. and Pronk, J. T. (2001). Stoichiometry and compartmentation of NADH metabolism in Saccharomyces cerevisiae. FEMS Microbiol Rev 25, 15-37.

Blomberg A, Adler L. 1989. Roles of glycerol and glycerol-3-phosphate dehydrogenase (NAD+) in acquired osmotolerance of Saccharomyces cerevisiae. J Bacteriol 171(2), 1087-92.

Bothast, R. J. and Schlicher, M. A. (2005). Biotechnological processes for conversion of corn into ethanol. Appl Microbiol Biotechnol 67, 19-25.

Bradford M M. 1976. A rapid and sensitive method for the quantitation of microgram quantities of protein utilizing the principle of protein-dye binding. Anal Biochem 72, 248-54.

Bro, C., Regenberg, B., Forster, J. and Nielsen, J. (2005). In silico aided metabolic engineering of Saccharomyces cerevisiae for improved bioethanol production. Metab Eng.

Ciriacy M. 1975. Genetics of alcohol dehydrogenase in Saccharomyces cerevisiae. II. Two loci controlling synthesis of the glucose-repressible ADH II. Mol Gen Genet. 138(2), 157-64.

Ferreira, C., van Voorst, F., Martins, A., Neves, L., Oliveira, R., Kielland-Brandt, M. C., Lucas, C. and Brandt, A. (2005). A member of the sugar transporter family, Stl1p is the glycerol/H+ symporter in Saccharomyces cerevisiae. Mol Biol Cell 16, 2068-76.

Gancedo C, Gancedo J M, Sols A. 1968. Glycerol metabolism in yeasts. Pathways of utilization and production. Eur J Biochem 5(2), 165-72.

Granath K, Modig T, Forsmark A, Adler L, Lidén G. (2005) The YIG1 (YPL201c) encoded protein is involved in regulating anaerobic glycerol metabolism in Saccharomyces cerevisiae. Yeast 22(16), 1257-68.

Gueldener, U., Heinisch, J., Koehler, G. J., Voss, D. and Hegemann, J. H. (2002). A second set of loxP marker cassettes for Cre-mediated multiple gene knockouts in budding yeast. Nucleic Acids Res 30, e23.

Guldener, U., Heck, S., Fielder, T., Beinhauer, J. and Hegemann, J. H. (1996). A new efficient gene disruption cassette for repeated use in budding yeast. Nucleic Acids Res 24, 2519-24.

Hohmann, S. (2002). Osmotic stress signaling and osmoadaptation in yeasts. Microbiol Mol Biol Rev 66, 300-72.

Izawa, S., Sato, M., Yokoigawa, K. and Inoue, Y. (2004). Intracellular glycerol influences resistance to freeze stress in Saccharomyces cerevisiae: analysis of a quadruple mutant in glycerol dehydrogenase genes and glycerol-enriched cells. Appl Microbiol Biotechnol 66, 108-14.

Jeffries, T. W. (2006). Engineering yeasts for xylose metabolism. Curr Opin Biotechnol 17, 320-6.

Karhumaa, K., Wiedemann, B., Hahn-Hagerdal, B., Boles, E. and Gorwa-Grauslund, M. F. (2006). Co-utilization of L-arabinose and D-xylose by laboratory and industrial Saccharomyces cerevisiae strains. Microb Cell Fact 5, 18.

Kohlwein, S. D., Daum, G., Schneiter, R. and Paltauf, F. (1996). Phospholipids: synthesis, sorting, subcellular traffic—the yeast approach. Trends Cell Biol 6, 260-6.

Lin, Y. and Tanaka, S. (2006). Ethanol fermentation from biomass resources: current state and prospects. Appl Microbiol Biotechnol 69, 627-42.

Lynd, L. R., van Zyl, W. H., McBride, J. E. and Laser, M. (2005). Consolidated bioprocessing of cellulosic biomass: an update. Curr Opin Biotechnol 16, 577-83.

Molin, M., Norbeck, J. and Blomberg, A. (2003). Dihydroxyacetone kinases in Saccharomyces cerevisiae are involved in detoxification of dihydroxyacetone. J Biol Chem 278, 1415-23.

Mullner, H. and Daum, G. (2004). Dynamics of neutral lipid storage in yeast. Acta Biochim Pol 51, 323-47.

Nevoigt, E., Fischer, C., Mucha, O., Matthaus, F., Stahl, U. and Stephanopoulos, G. (2007). Engineering promoter regulation. Biotechnol Bioeng 96, 550-8.

Nevoigt, E., Kohnke, J., Fischer, C. R., Alper, H., Stahl, U. and Stephanopoulos, G. (2006). Engineering of Promoter Replacement Cassettes for Fine-Tuning of Gene Expression in Saccharomyces cerevisiae. Appl Environ Microbiol 72, 5266-73.

Nevoigt, E., Pilger, R., Mast-Gerlach, E., Schmidt, U., Freihammer, S., Eschenbrenner, M., Garbe, L. and Stahl, U. (2002). Genetic engineering of brewing yeast to reduce the content of ethanol in beer. FEMS Yeast Res 2, 225-32.

Nevoigt, E. and Stahl, U. (1996). Reduced pyruvate decarboxylase and increased glycerol-3-phosphate dehydrogenase [NAD+] levels enhance glycerol production in Saccharomyces cerevisiae. Yeast 12, 1331-7.

Nevoigt, E. and Stahl, U. (1997). Osmoregulation and glycerol metabolism in the yeast Saccharomyces cerevisiae. FEMS Microbiol Rev 21, 231-41.

Nguyen, H. T., Dieterich, A., Athenstaedt, K., Truong, N. H., Stahl, U. and Nevoigt, E. (2004). Engineering of Saccharomyces cerevisiae for the production of L-glycerol 3-phosphate. Metab Eng 6, 155-63.

Nissen, T. L., Anderlund, M., Nielsen, J., Villadsen, J. and Kielland-Brandt, M. C. (2001). Expression of a cytoplasmic transhydrogenase in Saccharomyces cerevisiae results in formation of 2-oxoglutarate due to depletion of the NADPH pool. *Yeast* 18, 19-32.

Nissen, T. L., Hamann, C. W., Kielland-Brandt, M. C., Nielsen, J. and Villadsen, J. (2000a). Anaerobic and aerobic batch cultivations of *Saccharomyces cerevisiae* mutants impaired in glycerol synthesis. *Yeast* 16, 463-74.

Nissen, T. L., Kielland-Brandt, M. C., Nielsen, J. and Villadsen, J. (2000b). Optimization of ethanol production in *Saccharomyces cerevisiae* by metabolic engineering of the ammonium assimilation. *Metab Eng* 2, 69-77.

Norbeck, J. and Blomberg, A. (1997). Metabolic and regulatory changes associated with growth of *Saccharomyces cerevisiae* in 1.4 M NaCl. Evidence for osmotic induction of glycerol dissimilation via the dihydroxyacetone pathway. *J Biol Chem* 272, 5544-54.

Oliveira, R., Lages, F., Silva-Graca, M. and Lucas, C. (2003). Fps1p channel is the mediator of the major part of glycerol passive diffusion in *Saccharomyces cerevisiae*: artefacts and re-definitions. *Biochim Biophys Acta* 1613, 57-71.

Pahlman, A. K., Granath, K., Ansell, R., Hohmann, S, and Adler, L. (2001). The yeast glycerol 3-phosphatases Gpp1p and Gpp2p are required for glycerol biosynthesis and differentially involved in the cellular responses to osmotic, anaerobic, and oxidative stress. *J Biol Chem* 276, 3555-63.

Rigoulet, M., Aguilaniu, H., Averet, N., Bunoust, O., Camougrand, N., Grandier-Vazeille, X., Larsson, C., Pahlman, I. L., Manon, S, and Gustafsson, L. (2004). Organization and regulation of the cytosolic NADH metabolism in the yeast *Saccharomyces cerevisiae*. *Mol Cell Biochem* 256-257, 73-81.

Siderius, M., Van Wuytswinkel, O., Reijenga, K. A., Kelders, M. and Mager, W. H. (2000). The control of intracellular glycerol in *Saccharomyces cerevisiae* influences osmotic stress response and resistance to increased temperature. *Mol Microbiol* 36, 1381-90.

Valadi, A., Granath, K., Gustafsson, L. and Adler, L. (2004). Distinct intracellular localization of Gpd1p and Gpd2p, the two yeast isoforms of NAD+-dependent glycerol-3-phosphate dehydrogenase, explains their different contributions to redox-driven glycerol production. *J Biol Chem* 279, 39677-85.

Wojda, I., Alonso-Monge, R., Bebelman, J. P., Mager, W. H. and Siderius, M. (2003). Response to high osmotic conditions and elevated temperature in *Saccharomyces cerevisiae* is controlled by intracellular glycerol and involves coordinate activity of MAP kinase pathways. *Microbiology* 149, 1193-204.

---

The invention claimed is:

1. A method of modifying a yeast cell for the production of ethanol, the method comprising:

reducing, but not eliminating, glycerol-3-phosphate dehydrogenase 1, Gpd1, protein activity in the yeast cell and eliminating glycerol-3-phosphate dehydrogenase 2, Gpd2, protein activity in the yeast cell; or eliminating Gpd1 protein activity in the yeast cell and reducing, but not eliminating, Gpd2 protein activity in the yeast cell; or reducing, but not eliminating, both Gpd1 and Gpd2 protein activity in the yeast cell, wherein the reduction of Gpd1 protein activity and/or Gpd2 protein activity is achieved by reducing the expression of the GPD1 gene and/or the GPD2 gene by at least 50% compared to the expression of the GPD1 gene and/or the GPD2 gene in the unmodified wild type yeast cell and wherein the modified yeast cell has equivalent growth to that of an unmodified yeast cell under oxygen-limited conditions and an increased yield of ethanol.

2. The method as recited in claim 1, wherein the GPD1 gene and/or the GPD2 gene is expressed by a weak promoter that is operably linked to the GPD1 gene or to the GPD2 gene, wherein the weak promoter causes less than or equal to 20% transcription of the TEF1 promoter operably linked to the GPD1 gene or the GPD2 gene.

3. The method as recited in claim 2, wherein the weak promoter operably linked to the GPD1 gene or the GPD2 gene is a promoter according to SEQ ID NO 5 or SEQ ID NO 6.

4. The method as recited in claim 1, wherein the activity of the glycerol-3-phosphatase 1, Gpp1, protein and/or the glycerol-3-phosphatase 2, Gpp2, protein, is additionally reduced in the yeast cell, comprising:

reducing Gpp1 protein activity in the yeast cell and eliminating Gpp2 protein activity in the yeast cell; or eliminating Gpp1 protein activity in the yeast cell and reducing Gpp2 protein activity in the yeast cell; or reducing both Gpp1 protein and Gpp2 protein activity in the yeast cell, wherein the reduction of the activity of the Gpp1 protein and/or the Gpp2 protein is achieved by reducing the expression of the GPP1 and/or the GPP2 gene by at least 50% compared to the expression of the GPP1 gene and/or the GPP2 gene in a wild type yeast cell.

5. The method as recited in claim 4, wherein the GPP1 gene and/or the GPP2 gene is expressed by a weak promoter that is operably linked to the GPP1 gene or the GPP2 gene, wherein the weak promoter causes less than or equal to 20% transcription of the TEF1 promoter operably linked to the GPP1 gene or the GPP2 gene.

6. The method as recited in claim 5, wherein the promoter operably linked to the GPP1 gene or the GPP2 gene is a weak promoter according to SEQ ID NO 5 or SEQ ID NO 6.

7. A method for the production of ethanol, the method comprising
   providing a yeast cell modified as recited in claim 1; providing biomass; and
   growing the modified yeast cell in a presence of the biomass under conditions that allow for a production of ethanol.

* * * * *

SEQUENCE LISTING

<160> NUMBER OF SEQ ID NOS: 29

<210> SEQ ID NO 1
<211> LENGTH: 2176
<212> TYPE: DNA
<213> ORGANISM: Saccharomyces cerevisiae

<400> SEQUENCE: 1

```
aaaaaaagaa gaaaacagaa ggccaagaca gggtcaatga gactgttgtc ctcctactgt      60
ccctatgtct ctggccgatc acgcgccatt gtccctcaga aacaaatcaa acacccacac     120
cccgggcacc caaagtcccc acccacacca ccaatacgta aacggggcgc ccctgcagg     180 ccctcctgcg cgcggcctcc cgccttgctt ctctcccctt cctttcttt ttccagtttt     240 ccctattttg tccctttttc cgcacaacaa gtatcagaat gggttcatca aatctatcca     300
acctaattcg cacgtagact ggcttggtat tggcagtttc gtagttatat atatactacc     360
atgagtgaaa ctgttacgtt accttaaatt ctttctccct ttaattttct tttatcttac     420
tctcctacat aagacatcaa gaaacaattg tatattgtac accccccccc tccacaaaca     480
caaatattga taatataaag atgtctgctg ctgctgatag attaaactta acttccggcc     540
acttgaatgc tggtagaaag agaagttcct cttctgtttc tttgaaggct gccgaaaagc     600
ctttcaaggt tactgtgatt ggatctggta actggggtac tactattgcc aaggtggttg     660
ccgaaaattg taagggatac ccagaagttt tcgctccaat agtacaaatg tgggtgttcg     720
aagaagagat caatggtgaa aaattgactg aaatcataaa tactagacat caaaacgtga     780
aatacttgcc tggcatcact ctacccgaca atttggttgc taatccagac ttgattgatt     840
cagtcaagga tgtcgacatc atcgttttca acattccaca tcaatttttg ccccgtatct     900
gtagccaatt gaaaggtcat gttgattcac acgtcagagc tatctcctgt ctaaagggtt     960
ttgaagttgg tgctaaaggt gtccaattgc tatcctctta catcactgag gaactaggta    1020
ttcaatgtgg tgctctatct ggtgctaaca ttgccaccga agtcgctcaa gaacactggt    1080
ctgaaacaac agttgcttac cacattccaa aggatttcag aggcgagggc aaggacgtcg    1140
```

-continued

| | |
|---|---|
| accataaggt tctaaaggcc ttgttccaca gaccttactt ccacgttagt gtcatcgaag | 1200 |
| atgttgctgg tatctccatc tgtggtgctt tgaagaacgt tgttgcctta ggttgtggtt | 1260 |
| tcgtcgaagg tctaggctgg ggtaacaacg cttctgctgc catccaaaga gtcggtttgg | 1320 |
| gtgagatcat cagattcggt caaatgtttt tcccagaatc tagagaagaa acatactacc | 1380 |
| aagagtctgc tggtgttgct gatttgatca ccacctgcgc tggtggtaga acgtcaagg | 1440 |
| ttgctaggct aatggctact tctggtaagg acgcctggga atgtgaaaag gagttgttga | 1500 |
| atggccaatc cgctcaaggt ttaattacct gcaaagaagt tcacgaatgg ttggaaacat | 1560 |
| gtggctctgt cgaagacttc ccattatttg aagccgtata ccaaatcgtt tacaacaact | 1620 |
| acccaatgaa gaacctgccg gacatgattg aagaattaga tctacatgaa gattagattt | 1680 |
| attggagaaa gataacatat catactttcc cccactttt tcgaggctct tctatatcat | 1740 |
| attcataaat tagcattatg tcatttctca taactacttt atcacgttag aaattactta | 1800 |
| ttattattaa attaatacaa aatttagtaa ccaaataaat ataaataaat atgtatattt | 1860 |
| aaatttaaa aaaaaaatcc tatagagcaa aaggattttc cattataata ttagctgtac | 1920 |
| acctcttccg cattttttga gggtggttac aacaccactc attcagaggc tgtcggcaca | 1980 |
| gttgcttcta gcatctggcg tccgtatgta tgggtgtatt taaataata aacaaagtgc | 2040 |
| cacaccttca ccaattatgt ctttaagaaa tggacaagtt ccaaagagct tgcccaaggc | 2100 |
| tcgacaagga tgtactttgg aatatctata ttcaagtacg tggcgcgcat atgtttgagt | 2160 |
| gtgcacacaa taaagg | 2176 |

<210> SEQ ID NO 2
<211> LENGTH: 2323
<212> TYPE: DNA
<213> ORGANISM: Saccharomyces cerevisiae

<400> SEQUENCE: 2

| | |
|---|---|
| cttagcctct agccatagcc atcatgcaag cgtgtatctt ctaagattca gtcatcatca | 60 |
| ttaccgagtt tgtttttcctt cacatgatga agaaggtttg agtatgctcg aaacaataag | 120 |
| acgacgatgg ctctgccatt gttatattac gcttttgcgg cgaggtgccg atgggttgct | 180 |
| gaggggaaga gtgtttagct tacggaccta ttgccattgt tattccgatt aatctattgt | 240 |
| tcagcagctc ttctctaccc tgtcattcta gtatttttt tttttttttt tggttttact | 300 |
| tttttttctt cttgccttt tttcttgtta ctttttttct agtttttttt ccttccacta | 360 |
| agcttttcc ttgatttatc cttgggttct tctttctact cctttagatt ttttttttat | 420 |
| atattaattt ttaagtttat gtattttggt agattcaatt ctctttccct ttccttttcc | 480 |
| ttcgctcccc ttccttatca atgcttgctg tcagaagatt aacaagatac acattcctta | 540 |
| agcgaacgca tccggtgtta tatactcgtc gtgcatataa aattttgcct tcaagatcta | 600 |
| ctttcctaag aagatcatta ttacaaacac aactgcactc aaagatgact gctcatacta | 660 |
| atatcaaaca gcacaaacac tgtcatgagg accatcctat cagaagatcg gactctgccg | 720 |
| tgtcaattgt acatttgaaa cgtgcgccct tcaaggttac agtgattggt tctggtaact | 780 |
| gggggaccac catcgccaaa gtcattgcgg aaaacacaga attgcattcc catatcttcg | 840 |
| agccagaggt gagaatgtgg gttttgatg aaagatcgg cgacgaaaat ctgacggata | 900 |
| tcataaatac aagacaccag aacgttaaat atctacccaa tattgacctg ccccataatc | 960 |
| tagtggccga tcctgatctt ttacactcca tcaagggtgc tgacatcctt gttttcaaca | 1020 |
| tccctcatca atttttacca aacatagtca aacaattgca aggccacgtg gcccctcatg | 1080 |

```
taagggccat ctcgtgtcta aaagggttcg agttgggctc caagggtgtg caattgctat    1140
cctcctatgt tactgatgag ttaggaatcc aatgtggcgc actatctggt gcaaacttgg    1200
caccggaagt ggccaaggag cattggtccg aaaccaccgt ggcttaccaa ctaccaaagg    1260
attatcaagg tgatggcaag gatgtagatc ataagatttt gaaattgctg ttccacagac    1320
cttacttcca cgtcaatgtc atcgatgatg ttgctggtat atccattgcc ggtgccttga    1380
agaacgtcgt ggcacttgca tgtggtttcg tagaaggtat gggatggggt aacaatgcct    1440
ccgcagccat tcaaaggctg ggtttaggtg aaattatcaa gttcggtaga atgttttcc     1500 cagaatccaa agtcgagacc tactatcaag aatccgctgg tgttgcagat ctgatcacca    1560
cctgctcagg cggtagaaac gtcaaggttg ccacatacat ggccaagacc ggtaagtcag    1620
ccttggaagc agaaaaggaa ttgcttaacg gtcaatccgc caagggata atcacatgca     1680 gagaagttca cgagtggcta caaacatgtg agttgaccca agaattccca ttattcgagg    1740
cagtctacca gatagtctac aacaacgtcc gcatggaaga cctaccggag atgattgaag    1800
agctagacat cgatgacgaa tagacactct ccccccccct cccctctga tctttcctgt     1860 tgcctcttt  tccccaacc aatttatcat tatacacaag ttctacaact actactagta     1920
acattactac agttattata atttctatt ctcttttct ttaagaatct atcattaacg      1980
ttaatttcta tatatacata actaccatta tacacgctat tatcgtttac atatcacatc    2040
accgttaatg aaagatacga caccctgtac actaacacaa ttaaataatc gccataacct    2100
tttctgttat ctatagccct taaagctgtt tcttcgagct ttttcactgc agtaattctc    2160
cacatgggcc cagccactga gataagacg ctatgttagt cactactgac ggctctccag     2220
tcatttatgt gatttttag tgactcatgt cgcatttggc ccgttttttt ccgctgtcgc    2280
aacctatttc cattaacggt gccgtatgga agagtcattt aaa                      2323

<210> SEQ ID NO 3
<211> LENGTH: 1753
<212> TYPE: DNA
<213> ORGANISM: Saccharomyces cerevisiae

<400> SEQUENCE: 3
ggaaatccgt atcattttct cgcatacacg aacccgcgtg cgcctggtaa attgcaggat      60
tctcattgtc cggttttctt tatgggaata atcatcatca ccattatcac tgttactctt     120
gcgatcatca tcattaacat aatttttta acgctgtttg atgatggtat gtgcttttat     180
tgttccttac tcaccttttc ctttgtgtct tttaattttg accattttga ccattttgac    240 cttgatgat gtgtgagttc ctctttct ttttctttt cttttttcct tttttttct         300 tttcttactc tgttaatcac tttctttcct ttttgttcat attgtcgtct tgttcattt     360 cgttcaattg ataatgtata taaatctttc gtaagtatct cttgattgcc atttttttct    420
ttccaagttt cctgtgttatg aaacgtttca atgttttaaa atatatcaga acaacaaaag   480
caaatataca aaccatcgca atgcctttga ccacaaaacc tttatctttg aaaatcaacg    540
ccgctctatt cgatgttgac ggtaccatca tcatctctca accagccatt gctgctttct    600
ggagagattt cggtaaagac aagccttact tcgatgccga acacgttatt cacatctctc    660
acggttggag aacttacgat gccattgcca agttcgctcc agactttgct gatgaagaat    720
acgttaacaa gctagaaggt gaaatcccag aaaagtacgg tgaacactcc atcgaagttc    780
caggtgctgt caagttgtgt aatgcttga acgccttgcc aaaggaaaaa tgggctgtcg     840
ccacctctgg tacccgtgac atggccaaga atggttcga cattttgaag atcaagagac    900
```

```
cagaatactt catcaccgcc aatgatgtca agcaaggtaa gcctcaccca gaaccatact    960
taaagggtag aaacggtttg ggtttcccaa ttaatgaaca agacccatcc aaatctaagg   1020
ttgttgtctt tgaagacgca ccagctggta ttgctgctgg taaggctgct ggctgtaaaa   1080
tcgttggtat tgctaccact ttcgatttgg acttcttgaa ggaaaagggt tgtgacatca   1140
ttgtcaagaa ccacgaatct atcagagtcg gtgaatacaa cgctgaaacc gatgaagtcg   1200
aattgatctt tgatgactac ttatacgcta aggatgactt gttgaaatgg taattttctt   1260
ttatttttt  gataaaacta ctacgctaaa aataaaataa aaatgtatga tttccctcca   1320
tttccgacca attgtataat tttatatctg catgacttaa taatataata taatacttat   1380
aaaatacgaa tagaaaaatt taaaccgatg taatgcatcc ttttctttgt cgtcttcgga   1440
tgatctgccg tgacaggtgg ttcgcgcaaa tcaagctggt ttagagaatt taacacagaa   1500
ataaaaaagg aagattcaat cttcgttttt gttttatatc ttactataaa agtgtttttt   1560
tttagtacga cgagaagtta gagtaattat aaaaggaatg cttatttaaa tttatttctt   1620
agacttcttt tcagacttct tagcagcctc agtttgttcc ttaacgacct tcttaacaat   1680
cttttgttct tcaatcaaga aagctctgac gattctttcc ttgacacagt tggcacatct   1740
ggaaccaccg taa                                                      1753

<210> SEQ ID NO 4
<211> LENGTH: 1753
<212> TYPE: DNA
<213> ORGANISM: Saccharomyces cerevisiae

<400> SEQUENCE: 4
tctcaagtat tttggcacct cgccctgaac gaaaagctgg cactttgtcc ccagccaaac     60
tcttctctct aatatcgtct ttaacgacaa ggtaaaaaga tttctgcagt gttccgtctg    120
cgtcatcatc tgtgccccac aatccgcggc gtttccgtgt aagccgtcaa gtgaggactt    180
ttcggatgct gaaagaaagt acgctcggaa aaactacata gctgccccccc taaacgggcc    240
tcccacgtga cgtaaagtag gaataataag aagccaagtc gttctttttt attctaaata    300
agttcgtttc ttttgatgtt gtcatttttca gaaatatata tatatgcgct taaatacaca    360
agctaaaaca acatagttag gattgccaaa ggtttctttt ctactcaatt tggtctaact    420
cttttcatat taatagcgcc aaccagctag tgtttaccag atcagtggaa aaacataaaa    480
caataaaaac aatattcgga atgggattga ctactaaacc tctatctttg aaagttaacg    540
ccgctttgtt cgacgtcgac ggtaccatta tcatctctca accagccatt gctgcattct    600
ggagggattt cggtaaggac aaaccttatt tcgatgctga acacgttatc caagtctcgc    660
atggttggag aacgtttgat gccattgcta agttcgctcc agactttgcc aatgaagagt    720
atgttaacaa attgaagct gaaattccgg tcaagtacgg tgaaaaatcc attgaagtcc    780
caggtgcagt taagctgtgc aacgctttga acgctctacc aaaagagaaa tgggctgtgg    840
caacttccgg tacccgtgat atggcacaaa aatggttcga gcatctggga atcaggagac    900
caaagtactt cattaccgct aatgatgtca acagggtaa gcctcatcca gaaccatatc    960
tgaagggcag gaatggctta ggatatccga tcaatgagca agacccttcc aaatctaagg   1020
tagtagtatt tgaagacgct ccagcaggta ttgccgccgg aaaagccgcc ggttgtaaga   1080
tcattggtat tgccactact ttcgacttgg acttcctaaa ggaaaaggc tgtgacatca   1140
ttgtcaaaaa ccacgaatcc atcagagttg gcggctacaa tgccgaaaca gacgaagttg   1200
aattcatttt tgacgactac ttatatgcta aggacgatct gttgaaatgg taatcctcta   1260
```

| | |
|---|---|
| aaatcgaaca tatttgagta ataattctca gatacagtcc tattctatat tcgccacaaa | 1320 |
| acaagtaatg atgctaaaaa acgacacatt tataaaatca catcttattg attaaataaa | 1380 |
| tacgtagata gattttttt tttaaaacat atagtgtgct attatttctg actctgtctc | 1440 |
| atctcagaaa aataaatgat aaaaaaggaa gtaaaatcct taaacgttat caggttatta | 1500 |
| gcaacttgaa agtgacagga gccacaacgg attaaaattt aatttctagt aaagaaatgt | 1560 |
| caagaagagt ggttatcaca ggattgggct gtgtaacgcc gttgggaaga tcattaagtg | 1620 |
| agtcatgggg gaatctgctc tcttccaaaa atggactcac accaatcaca tctttgccca | 1680 |
| actataatga ggactacaaa ctcagagaaa aaagtatccc atcaacgata acagtgggga | 1740 |
| agattccaga gaa | 1753 |

<210> SEQ ID NO 5
<211> LENGTH: 401
<212> TYPE: DNA
<213> ORGANISM: Artificial
<220> FEATURE:
<223> OTHER INFORMATION: TEF1 promoter mutant 2

<400> SEQUENCE: 5

| | |
|---|---|
| acggctctaa agtgcttcgg ctcccccttt actcctccag gttttctcag actccgcgca | 60 |
| tcgccgtacc acctcaaagc ccccaagcgc agcataccaa atctcccctc tttcttcctc | 120 |
| tagggtgtca ctagttactc gtactaaggg tttggggaag gagaaagaga ccgcctcgtc | 180 |
| ttctttcctt cgtcgaaggg ggcaatagaa gttttatca tgtctccttt ccttgagaac | 240 |
| cttttcttcg atcttgttct ctttcgacgg cctcccgttg gtatttaggt taatgaacgg | 300 |
| tcttcaacct ctcaagtttc agtttccttt ctcccgtcct attacgaccc ttcttacttc | 360 |
| tcactcagta gaacgggagc atagcaatct aatccaagtt t | 401 |

<210> SEQ ID NO 6
<211> LENGTH: 401
<212> TYPE: DNA
<213> ORGANISM: Artificial
<220> FEATURE:
<223> OTHER INFORMATION: TEF1 promoter mutant 7

<400> SEQUENCE: 6

| | |
|---|---|
| atagcttcaa aatgtctcta ctccttttt actcttccag attttctcgg actccgcgca | 60 |
| ccgccgtacc acttcaaaac acccaagcac agcatactaa attccccctc ctccttcctc | 120 |
| tagggtgccg ttaattaccc gtactaaagg tttggaaaag gaaaagaga ccgcctcgtc | 180 |
| ccttttctt cgtcggagaa ggcaataaaa atttttatca cgtttctttc tcttgaaaac | 240 |
| ttttttttcg attttgttct ctttcgacga cctcccattg atatttgagt taacaaacgg | 300 |
| tcttcaattt ctcaagtttc agcttcattt ttcctgttct attacaactt tttttacttc | 360 |
| ttgctcattg gaaagaaagc atagcaatct aatctaagtt t | 401 |

<210> SEQ ID NO 7
<211> LENGTH: 20
<212> TYPE: DNA
<213> ORGANISM: Artificial
<220> FEATURE:
<223> OTHER INFORMATION: P9

<400> SEQUENCE: 7

| | |
|---|---|
| cccaaggcag gacagttacc | 20 |

```
<210> SEQ ID NO 8
<211> LENGTH: 21
<212> TYPE: DNA
<213> ORGANISM: Artificial
<220> FEATURE:
<223> OTHER INFORMATION: P10

<400> SEQUENCE: 8
agcaccagat agagcaccac a                                           21

<210> SEQ ID NO 9
<211> LENGTH: 21
<212> TYPE: DNA
<213> ORGANISM: Artificial
<220> FEATURE:
<223> OTHER INFORMATION: P11

<400> SEQUENCE: 9
ggaccaccaa cagcacctag t                                           21

<210> SEQ ID NO 10
<211> LENGTH: 21
<212> TYPE: DNA
<213> ORGANISM: Artificial
<220> FEATURE:
<223> OTHER INFORMATION: P12

<400> SEQUENCE: 10
gtaagcaact gttgtttcag a                                           21

<210> SEQ ID NO 11
<211> LENGTH: 401
<212> TYPE: DNA
<213> ORGANISM: Saccharomyces cerevisiae

<400> SEQUENCE: 11
atagcttcaa aatgtttcta ctcctttttt actcttccag attttctcgg actccgcgca    60
tcgccgtacc acttcaaaac acccaagcac agcatactaa atttcccctc tttcttcctc   120
tagggtgtcg ttaattaccc gtactaaagg tttggaaaag aaaaaagaga ccgcctcgtt   180
tctttttctt cgtcgaaaaa ggcaataaaa attttttatca cgtttctttt tcttgaaaat   240 ttttttttg atttttttct ctttcgatga cctcccattg atatttaagt taataaacgg   300
tcttcaattt ctcaagtttc agtttcattt ttcttgttct attacaactt tttttacttc   360
ttgctcatta gaaagaaagc atagcaatct aatctaagtt t                     401

<210> SEQ ID NO 12
<211> LENGTH: 62
<212> TYPE: DNA
<213> ORGANISM: Artificial
<220> FEATURE:
<223> OTHER INFORMATION: P29

<400> SEQUENCE: 12
atgcttgctg tcagaagatt aacaagatac acattcctta gatcccaata caacagatca    60
cg                                                                   62

<210> SEQ ID NO 13
<211> LENGTH: 60
<212> TYPE: DNA
<213> ORGANISM: Artificial
<220> FEATURE:
<223> OTHER INFORMATION: P30
```

```
<400> SEQUENCE: 13
cgatgtctag ctcttcaatc atctccggta ggtcttccat gttttattta ggttctatcg    60

<210> SEQ ID NO 14
<211> LENGTH: 22
<212> TYPE: DNA
<213> ORGANISM: Artificial
<220> FEATURE:
<223> OTHER INFORMATION: P33

<400> SEQUENCE: 14
ggtagattca attctctttc cc                                             22

<210> SEQ ID NO 15
<211> LENGTH: 22
<212> TYPE: DNA
<213> ORGANISM: Artificial
<220> FEATURE:
<223> OTHER INFORMATION: P34

<400> SEQUENCE: 15
aggcaacagg aaagatcaga gg                                             22

<210> SEQ ID NO 16
<211> LENGTH: 21
<212> TYPE: DNA
<213> ORGANISM: Artificial
<220> FEATURE:
<223> OTHER INFORMATION: GPP deletion primer

<400> SEQUENCE: 16
tgtgtgagtt cctctttcct t                                              21

<210> SEQ ID NO 17
<211> LENGTH: 20
<212> TYPE: DNA
<213> ORGANISM: Artificial
<220> FEATURE:
<223> OTHER INFORMATION: GPP deletion primer

<400> SEQUENCE: 17
tcaaaggcat tgcgatggtt                                                20

<210> SEQ ID NO 18
<211> LENGTH: 20
<212> TYPE: DNA
<213> ORGANISM: Artificial
<220> FEATURE:
<223> OTHER INFORMATION: GPP deletion primer

<400> SEQUENCE: 18
cgctaaggat gacttgttga                                                20

<210> SEQ ID NO 19
<211> LENGTH: 20
<212> TYPE: DNA
<213> ORGANISM: Artificial
<220> FEATURE:
<223> OTHER INFORMATION: GPP deletion primer

<400> SEQUENCE: 19
ctctaacttc tcgtcgtact                                                20
```

```
<210> SEQ ID NO 20
<211> LENGTH: 20
<212> TYPE: DNA
<213> ORGANISM: Artificial
<220> FEATURE:
<223> OTHER INFORMATION: GPP deletion primer

<400> SEQUENCE: 20
caagcaggaa atccgtatca                                              20

<210> SEQ ID NO 21
<211> LENGTH: 20
<212> TYPE: DNA
<213> ORGANISM: Artificial
<220> FEATURE:
<223> OTHER INFORMATION: GPP deletion primer

<400> SEQUENCE: 21
tcatatggag caatcccact                                              20

<210> SEQ ID NO 22
<211> LENGTH: 20
<212> TYPE: DNA
<213> ORGANISM: Artificial
<220> FEATURE:
<223> OTHER INFORMATION: GPP deletion primer

<400> SEQUENCE: 22
caagtgagga cttttcggat                                              20

<210> SEQ ID NO 23
<211> LENGTH: 20
<212> TYPE: DNA
<213> ORGANISM: Artificial
<220> FEATURE:
<223> OTHER INFORMATION: GPP deletion primer

<400> SEQUENCE: 23
gtagtcaatc ccattccgaa                                              20

<210> SEQ ID NO 24
<211> LENGTH: 20
<212> TYPE: DNA
<213> ORGANISM: Artificial
<220> FEATURE:
<223> OTHER INFORMATION: GPP deletion primer

<400> SEQUENCE: 24
ggacgatctg ttgaaatggt                                              20

<210> SEQ ID NO 25
<211> LENGTH: 21
<212> TYPE: DNA
<213> ORGANISM: Artificial
<220> FEATURE:
<223> OTHER INFORMATION: GPP deletion primer

<400> SEQUENCE: 25
cctgtccact ttcaagttgc t                                            21

<210> SEQ ID NO 26
<211> LENGTH: 391
<212> TYPE: PRT
<213> ORGANISM: Saccharomyces cerevisiae
```

<400> SEQUENCE: 26

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
                35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                    85                  90                  95

Pro Gly Ile Thr Leu Pro Asp Asn Leu Val Ala Asn Pro Asp Leu Ile
                100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

```
<210> SEQ ID NO 27
<211> LENGTH: 440
<212> TYPE: PRT
<213> ORGANISM: Saccharomyces cerevisiae

<400> SEQUENCE: 27

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys Cys His Glu Asp
    50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
    130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
    290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
    370                 375                 380
```

```
Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
            405                 410                 415

Gln Ile Val Tyr Asn Asn Val Arg Met Glu Asp Leu Pro Glu Met Ile
        420                 425                 430

Glu Glu Leu Asp Ile Asp Asp Glu
        435                 440

<210> SEQ ID NO 28
<211> LENGTH: 250
<212> TYPE: PRT
<213> ORGANISM: Saccharomyces cerevisiae

<400> SEQUENCE: 28

Met Pro Leu Thr Thr Lys Pro Leu Ser Leu Lys Ile Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile His Ile Ser His Gly Trp Arg Thr Tyr Asp Ala Ile Ala Lys
    50                  55                  60

Phe Ala Pro Asp Phe Ala Asp Glu Glu Tyr Val Asn Lys Leu Glu Gly
65                  70                  75                  80

Glu Ile Pro Glu Lys Tyr Gly Glu His Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Lys Lys Trp Phe Asp Ile
        115                 120                 125

Leu Lys Ile Lys Arg Pro Glu Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Phe Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250

<210> SEQ ID NO 29
<211> LENGTH: 250
<212> TYPE: PRT
<213> ORGANISM: Saccharomyces cerevisiae
```

```
<400> SEQUENCE: 29

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
                20                  25                  30

Phe Trp Arg Asp Phe Gly Lys Asp Lys Pro Tyr Phe Asp Ala Glu His
            35                  40                  45

Val Ile Gln Val Ser His Gly Trp Arg Thr Phe Asp Ala Ile Ala Lys
        50                  55                  60

Phe Ala Pro Asp Phe Ala Asn Glu Glu Tyr Val Asn Lys Leu Glu Ala
65                      70                  75                  80

Glu Ile Pro Val Lys Tyr Gly Glu Lys Ser Ile Glu Val Pro Gly Ala
                    85                  90                  95

Val Lys Leu Cys Asn Ala Leu Asn Ala Leu Pro Lys Glu Lys Trp Ala
                100                 105                 110

Val Ala Thr Ser Gly Thr Arg Asp Met Ala Gln Lys Trp Phe Glu His
                115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
                180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
        210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250
```